US005411993A

United States Patent [19]

Yamamoto et al.

[11] Patent Number: 5,411,993

[45] Date of Patent: May 2, 1995

[54] ANTI-INFLAMMATORY, STABLE AQUEOUS PREPARATION COMPRISING AZULENE SODIUM SULFONATE AND POLYHYDRIC ALCOHOL

[75] Inventors: Tokihiko Yamamoto, Nagoya; Tomoyuki Yamaoka, Kasugai; Yoshiaki Yoshida, Toyohashi; Kazuo Shin, Kodaira; Hiromitu Aonuma, Yokohama; Tutomu Tanaka, Tokyo, all of Japan

[73] Assignees: Nihon Tenganyaku Kenkyusho Co, Ltd.; Meiji Milk Prod. Co., Ltd., both of Japan

[21] Appl. No.: 89,581

[22] Filed: Jul. 12, 1993

[30] Foreign Application Priority Data

Jul. 13, 1992 [JP] Japan .................................. 4-185443

[51] Int. Cl.[6] ........................ A61K 31/015; A61K 9/10

[52] U.S. Cl. ...................................................... 514/766

[58] Field of Search .......................................... 514/766

[56] References Cited

FOREIGN PATENT DOCUMENTS

| | | |
|---|---|---|
| 58-13513 | 1/1983 | Japan . |
| 196816 | 11/1984 | Japan . |
| 63-48211 | 2/1988 | Japan . |
| 63-51341 | 3/1988 | Japan . |

OTHER PUBLICATIONS

Hamai et al., J. Am. Chem. Soc. 114(5), 6012–16. 1992.

*Primary Examiner*—Raymond Henley, III
*Assistant Examiner*—Phyllis G. Spivack
*Attorney, Agent, or Firm*—Bacon & Thomas

[57] ABSTRACT

Aqueous solution preparations which comprise azulene sodium sulfonate as an active ingredient and 20 w/v % or more of a polyhydric alcohol are disclosed wherein azulene sodium sulfonate is stable in the preparation for a prolonged period of time is suited for use in treating inflammation of the oral cavity and/or throat.

8 Claims, No Drawings

ANTI-INFLAMMATORY, STABLE AQUEOUS PREPARATION COMPRISING AZULENE SODIUM SULFONATE AND POLYHYDRIC ALCOHOL

BACKGROUND OF THE INVENTION

1. Field of the Invention

The present invention relates to stable aqueous solution preparations containing azulene sodium sulfonate as an active ingredient, which are suited for use as a preventive or therapeutic medicine for inflammatory diseases in digestive organs, oral cavity and throat, otolaryngology, ophthalmology, etc., and which can be used easily and hygienically.

2. Discussion of the Background

Azulene sodium sulfonate is found in an extract of the plant camomile (Matricaria Chamomilla L.) which belongs to the Asteraceae originated in the South and East Europe. As a folk medicine, it has long been used to cure a variety of inflammatory diseases. Currently, it is widely used as an anti-inflammatory agent to be incorporated in medicines for treating gastritis and gastric ulcer, mouthwashes, oral preparations, eye drops and the like.

Azulene sodium sulfonate is generally formed into solids such as tablets, lozenges, granule, powder, and the like, with an exception of eye drops. Drugs for internal use are orally administered as they are, while mouthwashes are prepared by dissolving the solid drug in water just before dosing. This is primarily due to the fact that azulene sodium sulfonate is unstable and easily degraded in the aqueous solution as time passes and under diffused light.

Eye drops, which are the only preparation marketed in liquids, usually contain adjuvants such as thiosulfate (antioxidizing agent) and EDTA (chelating agent), and are provided in expensive air-tight containers. Some of the adjuvants cannot be used as ingredients of drugs for oral administration. Moreover, the stability of eye drop preparations is not sufficiently good.

Reflecting the increased number of patients suffering from oral diseases typified by stomatitis and sore throat, which may possibly be due to the overpopulation and environmental pollution, there has recently been a growing demand for OTC (over-the-counter) drugs which are easily applied to the oral cavity/throat and are free from adverse side effects. As a solution, lozenge or dissolving-on-use type preparations containing azulene sodium sulfonate are considered. However, they are not necessarily satisfactory in that the active ingredient, azulene sodium sulfonate, will not successfully reach the affected area via lozenge, while dissolving-on-use type will require water and a glass, which makes the whole process troublesome and non-hygienic.

Accordingly, there is still a demand for an aqueous solution preparation of azulene sodium sulfonate suited for the internal administration or the oral cavity/throat application. So far before the present invention, however, it has been considered difficult to industrially provide such an aqueous preparation containing azulene sodium sulfonate as an active ingredient, because the sulfonate is unstable in an aqueous solution, and hence, aqueous solution preparations of azulene sodium sulfonate have never existed.

SUMMARY OF THE INVENTION

Accordingly, it is one object of the present invention is to provide a stable aqueous solution preparation containing azulene sodium sulfonate as an active ingredient.

It is another object of the present invention to provide an aqueous solution preparation which comprises azulene sodium sulfonate as an active ingredient and 20 w/v % or more of a polyhydric alcohol.

These and other objects, features and advantages of the present invention will become apparent from the following description.

DETAILED DESCRIPTION OF THE INVENTION AND PREFERRED EMBODIMENTS

The present inventors have conducted extensive studies and have found that when an aqueous solution preparation of azulene sodium sulfonate contains a polyhydric alcohol as a solubilizer, the stability of azulene sodium sulfonate is maintained for an unexpectedly prolonged period of time.

The polyhydric alcohol is known to be a highly safe substance. Examples of the polyhydric alcohol useful in the present invention include glycerin, glycols and sugaralcohols. As for glycols, mention may be given to propylene glycols and the like. As for sugaralcohols, mention may be given to sorbitol, xylitol and the like. Among them, glycerin is particularly preferred from the viewpoint of the excellent stabilizing ability for azulene sodium sulfonate.

These polyhydric alcohols are contained in the aqueous solution preparation according to the present invention in amounts of 20 w/v % (hereinafter simply referred to as %) or more, preferably from 20 to 90%, and more preferably from 30 to 80%. Amounts less than 20% are not preferred because azulene sodium sulfonate cannot be maintained stably for a prolonged period of time.

The present aqueous solution preparation can contain optional ingredients so long as they do not impede the effects of the present invention. Examples of such optional ingredients include flavors, buffers, preservatives and stabilizers.

The aqueous solution preparation according to the present invention can be prepared by conventional methods, for instance, by blending a mixture of azulene sodium sulfonate and a polyhydric alcohol with a buffer, preservative, sterile distilled water, etc. Although no particular limitation is imposed on the concentration of azulene sodium sulfonate, it is preferred that the concentration be from 0.02–0.06%. Moreover, the pH of the aqueous solution preparation according to the present invention is preferably adjusted to fall within the range from 7–9.

The thus-obtained aqueous solution preparation of the present invention is useful as medicines for internal administration, oral cavity/throat application or nasal drops. In case of the oral cavity/throat application, it is preferred that the preparation be placed in a handy container which is so designed that one can apply the right amount of dose by directly jet-spraying onto the affected part. This combination of the aqueous solution preparation of azulene sodium sulfonate and the handy container for jet-spraying is especially advantageous in the treatment of inflammation of the oral cavity and pharyngitis, because water is no more required.

EXAMPLES

The present invention will now be described more specifically by way of examples, which however, should not be construed as limiting the invention thereto.

Example 1

(1) Aqueous 0.02% solutions of azulene sodium sulfonate were added with 80% polyhydric alcohols (glycerin, sorbitol, xylitol and propyleneglycol, separately) to prepare aqueous test solutions. Each of the test solutions was charged in a 15 ml polyethylene container, and stored in a thermo-hydrostat under the conditions of 40°±1° C. and 75°±5% RH (light shielded). The content of azulene sodium sulfonate was measured by an auto-recording spectrophotometer (manufactured by Shimazu, UV-240) at the wavelength of 570 nm as time elapsed. The residual rate was calculated counting the absorbance measured just preceding the storage as 100%. The results are shown in Table 1. The data show that the addition of polyhydric alcohol gives significantly higher stabilizing effect when compared to the absence of polyhydric alcohol. Specifically, glycerin exhibited outstanding and remarkable stabilizing effect, indicating that azulene sodium sulfonate should be stable over 3 years when stored at the normal ambient temperature.

TABLE 1

| | Just before storage | After 2 wks | After 4 wks | After 6 wks | After 8 wks |
|---|---|---|---|---|---|
| Glycerin | 100.0 | 100.0 | 100.0 | 99.2 | 98.7 |
| Sorbitol | 100.0 | 93.7 | 86.7 | 82.6 | 80.0 |
| Xylitol | 100.0 | 95.9 | 90.0 | 86.3 | 82.2 |
| Propylene glycol | 100.0 | 96.8 | 90.6 | 85.7 | 81.0 |
| (non addition) | 100.0 | 92.6 | 85.2 | 75.9 | 66.7 |

(2) Aqueous 0.02% azulene sodium sulfonate solutions were added with 0%, 20%, 40%, 60% or 80% of glycerin, respectively, and charged in transparent glass vials. Stability against the light was investigated by following the similar procedure as described in (1) above. The residual rate was calculated counting the absorbance just before the storage as 100%. The results are shown in Table 2. The data show that the stabilizing effect is more significant as the concentration of glycerin increases. When 80% of glycerin was added, the residual rate after 4 hour storage was 94.2% indicating very high stability, whereas absence of glycerin and 20% of glycerin gave the residual rates of only 54.8% and 72.4%, respectively. Thus, the stabilizing activity of glycerin was statistically meaningful.

TABLE 2

| | Exposure to the sunlight | | | | |
|---|---|---|---|---|---|
| | 0 hr | 1 hr | 2 hrs | 3 hrs | 4 hrs |
| Glycerin 0% | 100.0 | 81.2 | 72.1 | 64.5 | 54.8 |
| Glycerin 20% | 100.0 | 91.3 | 84.3 | 78.9 | 72.4 |
| Glycerin 40% | 100.0 | 94.8 | 91.4 | 87.4 | 83.0 |
| Glycerin 60% | 100.0 | 97.5 | 96.5 | 93.7 | 90.9 |
| Glycerin 80% | 100.0 | 97.7 | 97.0 | 95.7 | 94.2 |

(3) Aqueous 0.02% azulene sodium sulfonate solutions added with 0%, 20%, 40%, 60% and 80% of glycerin, respectively, were stored in a thermo-hydrostat under the same severe conditions as described in (1) to study changes in the residual rate as time elapses over 12 weeks. As a result, higher concentration of glycerin provided more significant stabilizing effect as shown in Table 3. Practically, it is advisable that azulene sodium sulfonate should be maintained at a residual rate of over 90% after 12 weeks of storage (equivalent to 1.5 year storage at room temperature). From this standard, it is determined that the minimal concentration of glycerin to be added is 20% in a practical use.

TABLE 3

| | Just before Storage | after 4 w storage | after 8 w storage | after 12 w storage |
|---|---|---|---|---|
| Glycerin 0% | 100.0 | 85.2 | 66.7 | 44.8 |
| Glycerin 20% | 100.0 | 98.2 | 95.0 | 91.4 |
| Glycerin 40% | 100.0 | 99.2 | 97.0 | 94.0 |
| Glycerin 60% | 100.0 | 100.0 | 98.4 | 97.2 |
| Glycerin 80% | 100.0 | 100.0 | 98.7 | 97.4 |

Storage conditions: 40°±1° C., 75±5% RH (light shielded)

Example 2

| Formulation: | |
|---|---|
| Azulene sodium sulfonate | 0.02 g |
| Glycerin | 25 |
| Sodium hydrogencarbonate | 0.2 |
| Sodium sorbate | 0.1 |
| Flavor | suitable amount |

The above ingredients were mixed and added with sterile distilled water to dissolve and to make the total quantity of 100 ml. The pH of the solution was adjusted to approximately 8.2. Subsequent to the aseptic filtration, the solution was charged in an air-tight container.

Example 3

| Formulation: | |
|---|---|
| Azulene sodium sulfonate | 0.02 g |
| Glycerin | 35 |
| Sodium citrate | 0.2 g |
| Ethanol (95%) | 15 ml |
| L-menthol | 0.01 ml |

The above ingredients were mixed and added with sterile distilled water to dissolve and to make the total quantity of 100 ml. The pH of the solution was adjusted to approximately 8.4. Subsequent to the aseptic filtration, the solution was charged in an air-tight container.

Example 4

| Formulation: | |
|---|---|
| Azulene sodium sulfonate | 0.04 g |
| Glycerin | 80 |
| Boric Acid | 1 |
| Borax | 0.4 |
| Paraoxypropyl benzoate | 0.07 |
| Paraoxymethyl benzoate | 0.13 |

The above ingredients were mixed and added with sterile distilled water to dissolve and to make the total quantity of 100 ml. The pH of the solution was adjusted to approximately 7.8. Subsequent to the aseptic filtration, the solution was charged in an air-tight container.

Example 5

| Formulation: | |
|---|---|
| Azulene sodium sulfonate | 0.02 g |
| Sorbitol | 75 |
| Boric acid | 1 |
| Borax | 0.4 |
| Ethylenediamine tetraacetate | 0.05 |
| Sodium thiosulfate | 0.2 |

The above ingredients were mixed and added with sterile distilled water to dissolve and to make the total quantity of 100 ml. The pH of the solution was adjusted to approximately 8.3. Subsequent to the aseptic filtration, the solution was charged in a nasal spray container.

As described herein above in this specification, the present invention provides an aqueous solution preparation containing azulene sodium sulfonate as an active ingredient, which is stable over a prolonged period of time, is highly safe, and is suited for handy and hygienic use in the treatment of the oral cavity and throat.

What is claimed is:

1. An aqueous solution preparation for topical application to treat inflammation of the oral cavity or throat which comprises 0.02 to 0.06 w/v % of azulene sodium sulfonate as an active ingredient and 20 w/v % or more of a polyhydric alcohol selected from the group consisting of glycerin, sorbitol and xylitol.

2. The preparation as defined in claim 1, wherein the amount of the polyhydric alcohol is from 20 to 90 w/v %.

3. The preparation as defined in claim 2, wherein the polyhydric alcohol is present in the amount of 30–80 w/v %.

4. The preparation as defined in claim 2 further comprising an ingredient selected from the group consisting of flavors, buffers, preservatives, stabilizers and water.

5. The preparation as defined in claim 1, wherein the polyhydric alcohol is glycerin.

6. The preparation as defined in claim 1, wherein the polyhydric alcohol is selected from the group consisting of sorbitol and xylitol.

7. The preparation as defined in claim 1, wherein the pH of the composition is in the range of 7–9.

8. A method for the treatment of inflammation of the oral cavity or throat, which comprises applying the preparation of claim 1 to the oral cavity or throat.

* * * * *